US007137359B1

(12) United States Patent
Braden

(10) Patent No.: US 7,137,359 B1
(45) Date of Patent: Nov. 21, 2006

(54) ESTRUS DETECTOR

(76) Inventor: Joe T. Braden, 13428 Farm Rd., #269, Pickton, TX (US) 75421

( * ) Notice: Subject to any disclaimer, the term of this patent is extended or adjusted under 35 U.S.C. 154(b) by 0 days.

(21) Appl. No.: 11/269,280

(22) Filed: Nov. 8, 2005

(51) Int. Cl.
*A61B 10/00* (2006.01)
*A01K 21/00* (2006.01)
*A01K 29/00* (2006.01)

(52) U.S. Cl. ........................ 119/854; 119/860; 600/551

(58) Field of Classification Search ................ 119/838, 119/850, 854, 174, 14.03, 856, 14.01, 858, 119/14.18, 860, 653, 654, 656; 600/551
See application file for complete search history.

(56) References Cited

U.S. PATENT DOCUMENTS 3,076,431 A 2/1963 Rule et al.
3,158,133 A 11/1964 Larson
3,158,134 A 11/1964 Larson
3,603,291 A 9/1971 Baker
3,842,802 A 10/1974 Lang et al.
3,844,273 A 10/1974 Polson
3,942,475 A 3/1976 Wassilieff et al.
4,206,766 A 6/1980 Bielka
4,224,949 A 9/1980 Scott et al.
4,239,018 A 12/1980 Griffin et al.
4,247,758 A 1/1981 Rodrian
4,411,274 A 10/1983 Wright
4,455,610 A 6/1984 Rodrian
4,503,808 A 3/1985 McAlister
4,635,587 A 1/1987 Leonardo
4,685,421 A 8/1987 Colburn, Jr.
4,696,258 A 9/1987 Magrath et al.
4,784,155 A 11/1988 Mills
4,846,106 A 7/1989 Leonardo
4,895,165 A 1/1990 Blair
5,111,799 A 5/1992 Senger et al.
5,542,431 A 8/1996 Starzl et al.
5,566,679 A 10/1996 Herriott
5,839,390 A 11/1998 Meads
5,881,673 A 3/1999 Beach et al.
6,342,041 B1 1/2002 Saint-Ramon et al.
6,467,430 B1 10/2002 Stampe
6,550,652 B1 4/2003 Whitaker
6,708,648 B1 3/2004 Stampe

FOREIGN PATENT DOCUMENTS

DE 19537048 A1 * 4/1997

* cited by examiner

*Primary Examiner*—Son T. Nguyen
(74) *Attorney, Agent, or Firm*—Locke Liddell & Sapp, LLP

(57) ABSTRACT

A pressure responsive estrus detector includes a housing having a first and second oppositely disposed side walls. A first interior wall is disposed within the housing and connected to the first side wall to create a first fluid chamber. The first interior wall has a top and bottom and an aperture disposed adjacent to the top. A second interior wall is disposed within the housing and connected to the second side wall to create a second fluid chamber. The second interior side wall is disposed adjacent to the first interior side wall. The second interior side wall has a top and bottom, aligned with the top and bottom of the first interior side wall. The second interior side wall includes an aperture disposed adjacent to the bottom. Fluid is disposed within the housing and flowable between the first and second fluid chambers via the first and second interior wall apertures by pressure applied to either one of said side walls by a mounting animal.

3 Claims, 2 Drawing Sheets

ESTRUS DETECTOR

TECHNICAL FIELD OF THE INVENTION

The present invention relates to the field of animal husbandry, and more particularly to a detector apparatus used to detect when an animal is in estrus (heat), and more particularly to a pressure responsive detector that can be reset, such that the detector is reusable.

BACKGROUND OF THE INVENTION

It is typically desirable in the field of animal husbandry to selectively breed livestock. This breeding may be done by mating selected animals, artificially inseminating an animal, or any other suitable method. However, any breeding method used entails determining when the animal is in heat in order for insemination to fertilize the animal. The heat cycle is of a short duration and insemination must occur during the cycle. The accurate detection of estrus is a long recognized problem. If a pregnant cow is inseminated she is very apt to abort her calf. This problem makes false positives very expensive. With a false negative, the hot cow's breeding is delayed 21 days. This problem costs the dairyman $3.00 per day or $60.00 on each false negative.

Typically, when an animal, for example, a cow, is not in heat, she will not allow herself to be mounted. Conversely, when a cow is in heat, the cow will show an increased tendency to stand and permit itself to be mounted by other animals for an appreciable time. When the mounted animal allows the mounting animal to remain for about five seconds, a "standing mount" has occurred and the cow is classified as in standing heat. This condition occurs in the early stages of estrus. The most frequent mountings occur by bulls, but mountings are also made by other cows. Accordingly, the repeated mounting of a cow by any other such animal is a good indication that the cow is in heat. Cows must be mounted at least three times before safe to breed.

The identification of cows in heat has traditionally been accomplished by observation, the cows seen to allow mounting by other cows being separated from the herd. While visual inspection and observation of a herd may be employed to identify and segregate females in heat, because the heat cycle is of short duration, such visual observation must be conducted multiple times during a day and accompanied by immediate segregation or marking of the animals to be inseminated. Visual observation of the herd, which is often widely dispersed, is typically inefficient. Further, if no indicating device is used, unless the herd is maintained under constant visual observation, the heat cycle may go undetected in many animals.

A variety of devices have been developed for indicating when an animal is in heat by detecting when the animal has been mounted. Automatic indicators have been used that are attached to the top rear section of the animal between the hip-bone and spine and are set off by other animals mounting the animal in heat. Typically, the indicators rely on the pressure exerted by the chest or brisket of the mounting animal. A common indicator of this type includes a passive apparatus including a reservoir of marker fluid which is compressed by the mounting pressure to discharge some or all fluid and thereby mark the mounted animal. Frequently, these devices suffer from incidental seepage of the marker fluid. This seepage can result in an undesirably short shelf-life of the product. Further, the prior devices involve complicated dye packet devices that are undesirably complex and expensive.

A need has thus arisen for a detector for determining when a cow is in heat, wherein the detector is automatic and accurate for indicating when a cow has been mounted for a time equal to or greater than a predetermined time. A need has further arisen for a pressure responsive estrus detector which can be reset whereby the detector can be reused multiple times.

SUMMARY OF THE INVENTION

In accordance with the present invention, a pressure responsive estrus detector adapted to be secured to a first animal in a position to be contacted by a mounting animal for indicating when the first animal is in heat is provided. The detector includes a housing having a first and second oppositely disposed side walls. A first interior wall is disposed within the housing and connected to the first side wall to create a first fluid chamber. The first interior wall has a top and bottom and an aperture disposed adjacent to the top. A second interior wall is disposed within the housing and connected to the second side wall to create a second fluid chamber. The second interior side wall is disposed adjacent to the first interior side wall. The second interior side wall has a top and bottom, aligned with the top and bottom of the first interior side wall. The second interior side wall includes an aperture disposed adjacent to the bottom. Fluid is disposed within the housing and flowable between the first and second fluid chambers via the first and second interior wall apertures by pressure applied to either one of said side walls by the mounting animal.

BRIEF DESCRIPTION OF THE DRAWINGS

For a more complete understanding of the present invention and for further advantages thereof, references is now made to the following Description of the Preferred Embodiments taken in conjunction with the accompanying Drawings in which.

DESCRIPTION OF THE PREFERRED EMBODIMENTS

Figure 1:
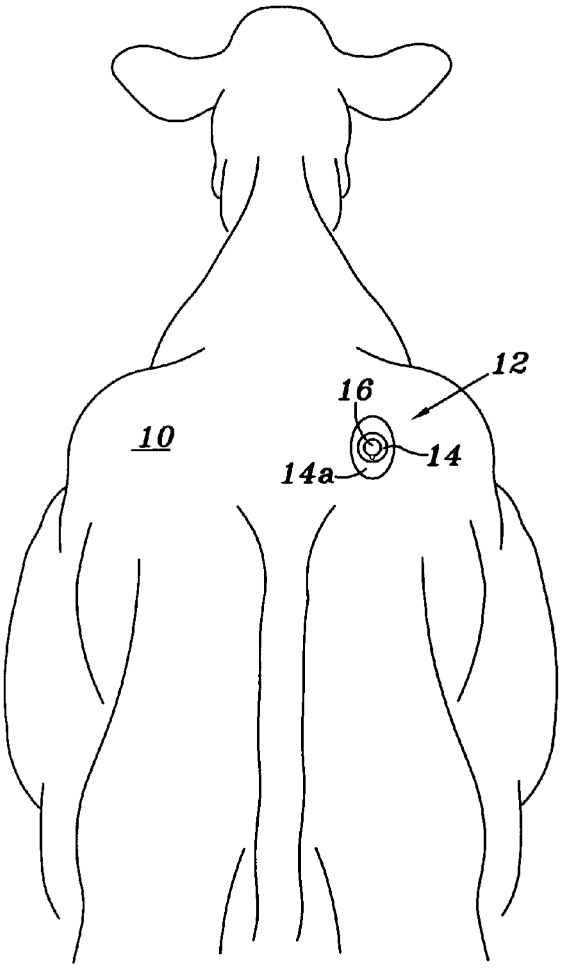
FIG. 1 is an illustration of a rear view of a cow including the present detector secured in position for use.

Referring to the Figures, FIG. 1 illustrates the rear view of a cow 10 on which the present estrus detector, generally identified by the numeral 12 is mounted. Detector 12 is positionally and selectively insertable within a holder 14 which is secured in a position near the backbone and above the rump of cow 10 using a double sided adhesive canvas pad 14*a*, it being understood that other methods of affixation can be utilized to affix holder 14 to cow 10. Detector 12 is mounted in a position such that when cow 10 is mounted, the relatively hard brisket of the mounting animal compresses detector 12 against the backbone area of cow 10, and such that gravity acts on the fluid contained within detector 12. Should this compression continue for a predetermined time, detector 12 will provide a visible indication which may be observed to indicate that cow 10 is in heat. The use of detector 12 makes it possible to mark cow 10 without the continued presence of an attendant to observe a herd, time the mounting, and mark cows.

Figure 2:
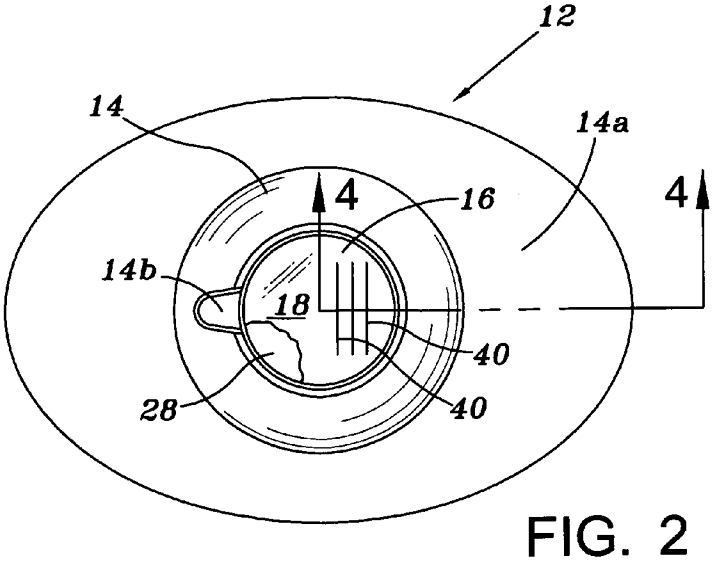
FIG. 2 is a top plan view of the present detector.
Figure 3:
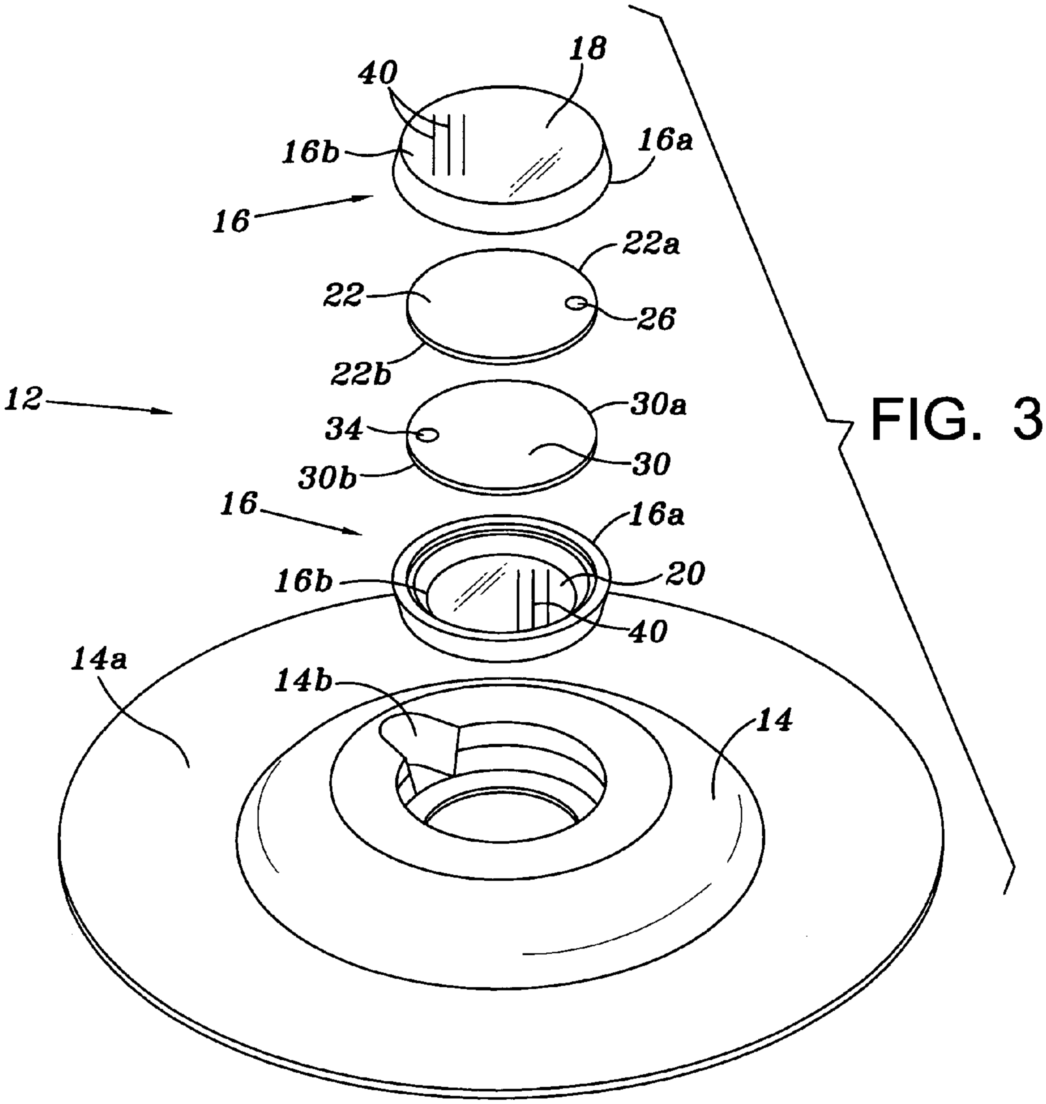
FIG. 3 is an exploded perspective view of the present detector illustrated in FIG. 2.
Figure 4:
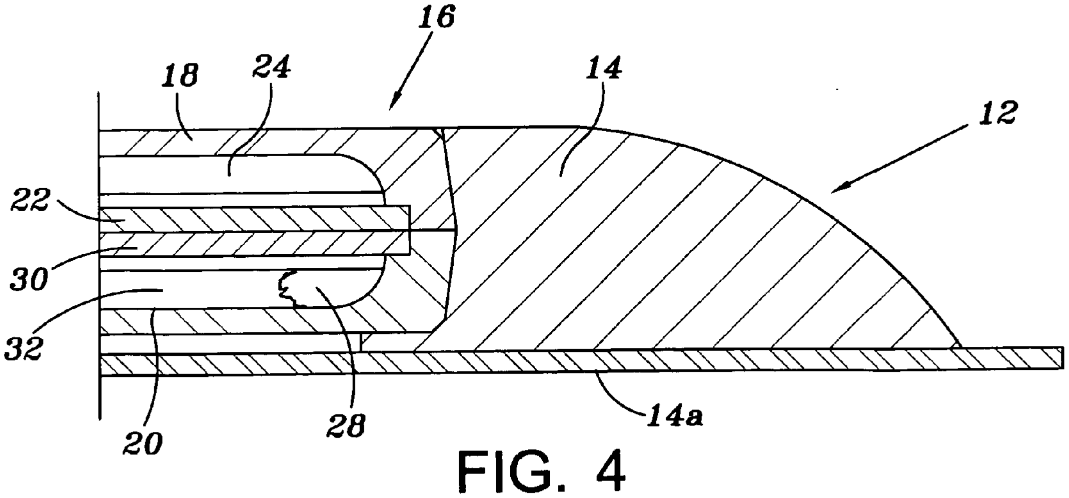
FIG. 4 is a cross-sectional view taken generally along section lines 4—4 of FIG. 2.

Referring to FIGS. 2–4, detector 12 includes a housing, generally identified by the numeral 16 having a top 16*a* and bottom 16*b*. Housing 16 is positioned within holder 14 in one of two positions with top 16*a* toward the head of cow 10 or with bottom 16*b* positioned toward the head of cow 10. Housing 16 includes a first side wall 18 and second side wall 20 which are joined together to form a fluid tight enclosure for a fluid 28. Side walls 18 and 20 comprise a transparent material of plastic, or other suitable flexible material. Side walls 18 or 20 come in contact with the mounting animal, mounting cow 10.

Disposed within housing 16 and adjacent to first side wall 18 is a first interior wall 22. Interior wall 22 and side wall 18 are sealed to form a first fluid chamber 24 within housing 16. First interior wall 22 includes a top 22*a* and a bottom 22*b*. Adjacent to top 22*a* of first interior wall 22 is an aperture 26. Aperture 26 allows fluid 28 present within housing 16 to flow into and out of chamber 24. Fluid 28 may comprise, for example, colored ethylene glycol.

Also disposed within housing 16 is a second interior wall 30. Second interior wall 30 and second side wall 20 are sealed to form a second fluid chamber 32 disposed within housing 16. Second interior wall 30 includes a top 30*a* and a bottom 30*b*. Disposed adjacent to bottom 30*b* of second interior wall 30 is an aperture 34. Aperture 34 allows fluid 28 to flow into and out of chamber 32 within housing 16.

Fluid 28 flows within housing 16 from chamber 32 outwardly via aperture 34 and into chamber 24 via aperture 26 upon pressure being applied to first side wall 18. Conversely, when fluid is present within chamber 24, fluid flows outwardly from aperture 26 into chamber 32 via aperture 34 when pressure is applied to side wall 20. The present detector 14 is reusable do to the ability of fluid to flow between chambers 24 and 32, and the selective repositioning of housing 16 within holder 14.

In operation, with housing 16 mounted within holder 14 such that top 16*a* is positioned in the direction of the head of cow 10, fluid is retained within the bottom portion of second chamber 32. Second side wall 20 is positioned adjacent to cow 10, and first side wall 18 is exposed to pressure exerted by the mounting cow. When pressure is exerted on first side wall 18, fluid is forced out of second fluid chamber 32 via aperture 34, and enters first fluid chamber 24 via aperture 26 to collect at the bottom portion of fluid chamber 24. Each time the mounting cow exerts pressure on first side wall 18, a predetermined amount of fluid flows from second chamber 32 into first chamber 24 thereby allowing first fluid chamber 24 to fill up, and thereby provide an indication of the number of times cow 10 has been mounted. First side wall 18 and second side wall 20 include measurement indicia 40 which can be used to provide a visual indication of the number of times cow 10 has been mounted. Fluid flowing into first fluid chamber 24 fills first fluid chamber 24 from the bottom near indicia 40 towards the top 16*a* of housing 16.

When cow 10 has been mounted a sufficient number of times, all or most of fluid 28 will be depleted from second fluid chamber 32 and will be stored within first fluid chamber 24. When it is desired to reset detector 12 for reuse, detector 12 is removed from holder 14 via slot 14*b* and replaced into holder 14 such that bottom 16*b* of housing 16 is positioned towards the head of cow 10. In this position, fluid 28 is positioned in the bottom portion of fluid chamber 24, first side wall 18 is positioned adjacent to cow 10, and second side wall 20 is positioned to receive pressure from a mounting cow. As cow 10 is mounted, fluid 28 flows from first fluid chamber 24 via aperture 26 into second fluid chamber 32 via aperture 34. Second fluid chamber 32 now fills as cow 10 is mounted due to pressure being exerted by the mounting cow on second side wall 20 each time cow 10 is mounted. Detector 12 is reusable because fluid 28 flows between chambers 24 and 32. Detector 12 is reset by presenting a fluid chamber 24 or 32 in an empty condition for contact with the mounting cow, such that fluid is forced from the full chamber 24 or 32 adjacent to cow 10 when pressure is exerted on the opposing, empty, chamber 24 or 32 by the mounting cow.

Other alteration and modification of the invention will likewise become apparent to those of ordinary skill in the art and upon reading the present disclosure, and it is intended that the scope of the invention disclosed herein be limited only by the broadest interpretation of the appended claims to which the inventor is legally entitled.

I claim:

1. A pressure responsive estrus detector adapted to be secured to a first animal in a position to be contacted by a mounting animal for indicating when the first animal is in heat, the detector comprising:

a housing having first and second oppositely disposed side walls;

a first interior wall disposed within said housing and connected to said first side wall to create a first fluid chamber, said first side wall having a top and a bottom and an aperture disposed adjacent said top;

a second interior wall disposed within said housing and connected to said second side wall to create a second fluid chamber, said second interior wall disposed adjacent to said first interior wall, said second interior wall having a top and bottom aligned with said top and said bottom of said first interior wall, and said second interior wall having an aperture disposed adjacent said bottom; and fluid disposed within said housing and flowable between said first and said second fluid chambers via said first and said second interior wall apertures by pressure applied to one of said side walls by the mounting animal.

2. The detector of claim 1 wherein the detector is adapted to be reset to a condition prior to mounting of the first animal by the mounting animal whereby the detector can be reused, such that when the detector is secured to the first animal and said second side wall is disposed adjacent to the first animal, fluid is contained in said second chamber prior to the first animal being mounted by the mounting animal and fluid flows into said first chamber upon pressure being applied to said first side wall by the mounting animal; and such that the detector is reset by disposing said first side wall adjacent to the first animal, such that fluid contained within said first chamber flows from said first chamber to said second chamber upon pressure being applied to said second side wall by the mounting animal.

3. The detector of claim 1 wherein said side walls include fluid measuring indicia to provide a visual indication of the number of times the first animal has been mounted.

* * * * *